United States Patent [19]  [11] Patent Number: 4,701,177
Ellis et al.  [45] Date of Patent: Oct. 20, 1987

[54] THREE-DIMENSIONAL SHAPED FEMININE PAD WITH NARROW, ABSORBENT CENTER AND WINGED EDGES

[75] Inventors: Louise C. Ellis; Anne M. Fahrenkrug, both of Appleton; Julie T. Basten, Green Bay; James D. Milner, Appleton, all of Wis.

[73] Assignee: Kimberly-Clark Corporation, Neenah, Wis.

[21] Appl. No.: 818,438

[22] Filed: Jan. 13, 1986

[51] Int. Cl.$^4$ ............................................ A61F 13/18
[52] U.S. Cl. ................................ 604/385 A; 604/358; 604/379
[58] Field of Search ................. 604/385.1, 385.2, 366, 604/370, 379

[56] References Cited

U.S. PATENT DOCUMENTS 3,371,668  3/1968  Johnson .
3,805,790  4/1974  Kaczmarzyk et al. .
4,333,782  6/1982  Pieniak .
4,397,644  8/1983  Matthews et al. .
4,433,972  2/1984  Malfitano .
4,490,147  12/1984  Pierce .
4,490,148  12/1984  Beckestrom .

FOREIGN PATENT DOCUMENTS

0091412  10/1983  European Pat. Off. .
0164435  12/1985  European Pat. Off. .
0167931  1/1986   European Pat. Off. .
2142241  1/1985   United Kingdom .
2142541  1/1985   United Kingdom .
2156681  10/1985  United Kingdom .

Primary Examiner—C. Fred Rosenbaum
Assistant Examiner—Sherri E. Vinyard
Attorney, Agent, or Firm—Paul A. Leipold; Donald L. Traut; Jeremiah J. Duggan

[57] ABSTRACT

The invention is generally accomplished by providing an elongated, curved, better-fitting absorbent pad for absorption of bodily excretions comprising a liquid-impermeable backing member, an absorbent inner member and a liquid-permeable body-side member. The absorbent member is shaped generally in a manner that provides a narrower middle portion of absorbent material. The middle portion also in the preferred embodiment is somewhat thicker than the absorbent portions at the ends of the pad. The pad is provided with upstanding side portions in the middle of each long edge in the area where the absorbent is narrower. The pad further is curved so as to generally conform to the pudendum.

17 Claims, 14 Drawing Figures

FIG. 14

THREE-DIMENSIONAL SHAPED FEMININE PAD WITH NARROW, ABSORBENT CENTER AND WINGED EDGES

TECHNICAL FIELD

This invention relates to absorbent pads for external application. It more particularly relates to an elongated cup-shaped garment particularly adapted for menstrual use as a catamenial device.

BACKGROUND ART

The present invention relates to an absorbent product, such as a sanitary napkin, comprising an absorbent body and a jacket enclosing said body, said jacket comprising a fluid-permeable layer located closest to the user when in use and a fluid-impermeable layer disposed on the opposite side—the back—of the absorbent body.

Leakage to the side has been a problem when using sanitary napkins. This has been a problem in all types of sanitary napkins, both the older types, i.e. thick and wide napkins, and in more modern types, e.g. so-called body-shaped napkins, which vary in thickness along their lengths and are relatively narrow in the midsection where they are thickest.

Sanitary napkins of the older, uniformly thick types are often greatly deformed when used quite simply because they are too large and not fitted to the shape of the human body. They also are not resilient and deform as the body of the wearer moves. Usually they are pressed together in the middle and bent along a longitudinal axis so that the front, the side in contact with the user, becomes convex with portions of the fluid-permeable layer facing out towards the sides at the same time as the fluid-impermeable back layer is more or less folded up resulting in a reduction in effective fluid-stopping surface. This means that fluid from the napkins can leak out through the folded out fluid-permeable front layer on both sides of the folded-up fluid-impermeable back layer. Leakage also is caused by the folding and shifting movement of the pad.

Attempts have been made to solve this problem by making the modern sanitary napkins so that when used they more closely follow the shape of the body and have their greatest absorption capacity where the need is greatest.

The modern sanitary napkins are not deformed especially much during use and are more comfortable. However, side leakage is still a substantial problem even in body-shaped napkins. On occasions when fluid discharge is great, experience has shown that not all the fluid has time to be absorbed; rather a portion can still leak out to the sides and over the longitudinal edges of the napkin.

Developments of the last few years, however, have made the napkins thinner and thinner. This has been made possible both by compressing the absorbent material, and by using high-absorbent material. Examples of such very thin and comfortable napkins are the thin sanitary pads with highly absorbent materials instead of sanitary napkins of the older thicker types.

For such thin napkins, side leakage is a problem as pads do not conform to the body. Since they are usually very thin, they must be relatively broad even in the middle, making them liable to be greatly deformed when used, unfortunately often resulting in edge leakage in this type of napkin as well.

Many different attempts have been made to eliminate the occurrence of lateral leakage. In thin napkins one example is to arrange a number of longitudinal compressed areas in the absorbent body for the purpose of rapidly spreading the fluid longitudinally. These compressed areas are, however, far from sufficient to satisfactorily eliminate edge leakage.

It is also known to further widen the fluid-impermeable back layer so as to cover, in addition to the back and side edges of the napkin, also a portion of the front side in contact with the user during use. In such a design the fluid already collected in the absorbent body is to be sure effectively enclosed, but instead there is the substantial disadvantage that the fluid-impermeable back layer folded in over the front side can cover a major portion of the napkin side facing the user when the napkin is deformed when used, whereby menstrual fluid can run directly out of the napkin on top of the portions of the back layer folded in over the front.

There have been proposed shaped pads for use as catamenial devices or incontinence use. European patent application No. 0091412—Widlund discloses a shaped pad. The pad of Widlund has elastic along the edges of the center portion of a generally rectangular pad. The elastic serves to shape the pad into a bowed shape with the elasticized edges extending upward beside the absorbent portion. Great Britain patent application No. 2,142,541—Buell discloses an elasticized waste containment garment, designed for incontinence use. This garment also has elasticized edges. In the Buell application the elastic extends almost the full length of the garment, and the elasticized edge portion not containing absorbent appears to be somewhat wider than that of Widlund. Another pad exhibiting elasticized edges is that disclosed in copending, coassigned application U.S. Ser. No. 629,297, Inventors Damico et al. titled "Bowed, Trough-Like Absorbent Pad."

There remains a need for a pad that fits the curve of the human body, is stationary during use, is comfortable to wear, effective, particularly against side leakage, and discreet. Thinner rectangular pads of the prior art are not of a shape that easily conforms to the body without bunching and being deformed. Therefore, there remains a need for an improved pad for catamenial use or for light incontinence use.

DISCLOSURE OF THE INVENTION

An object of this invention is to overcome disadvantages of prior body-conforming absorbent pads.

An additional object of this invention is to provide catamenial devices with improved protection against side leakage.

A further object of this invention is to provide a pad that is comfortable to wear and stays in place while worn.

A further additional object is to provide a catamenial pad that resists deformation while being worn.

These and other objects of the invention are generally accomplished by providing curved elongated absorbent pad for absorption of bodily excretions comprising a liquid-impermeable backing member, an absorbent inner member and a liquid-permeable body-side member. The absorbent member is shaped generally in a manner such as an hourglass or dog-bone shape that provides a narrower middle portion of absorbent material. The middle portion also in the preferred embodiment is somewhat thicker than the absorbent portions at the ends of the pad. The pad is provided with upstanding side portions in the middle of each long edge in the area where the absorbent is narrower. The preferred feminine pad further is curved so as to generally conform to the pudendum in the front and extend to about the area of the anus in the rear.

In the preferred form the pad, for feminine care, is formed from an elongated generally-rectangular backing sheet and body-side liner with elastic applied to the backing and liner in the area forming a flap outside of the narrowed portion of the hour-glass shaped absorbent. When the elastic is in relaxed (nonstretched) form, it draws the flaps upward such that they extend above the absorbent, and further shorten the pad causing the pad to curve.

MODES FOR CARRYING OUT THE INVENTION

The pad of the invention has numerous advantages over the prior art pads. The absorbent being less wide in the middle portion allows a better fit in the area of the vaginal opening while the wider end portions help to hold the pad in place as well as providing additional absorption and preventing leakage. The preferred form of the invention with upstanding walls and a thicker portion in the center provides a pad with superior absorbency and a high resistance to leakage. Further, the pad with the upstanding walls next to a narrow thick absorbent is comfortable with good liquid-holding capacity. Another advantage is that the pad of the invention, while shaped, is formed from a backing material and body-side liner that is generally rectangular, thereby minimizing difficulty and cost in the formation of the pad. These and other advantages of this invention will be apparent from the detailed description below and the description of the drawings.

Figure 1:
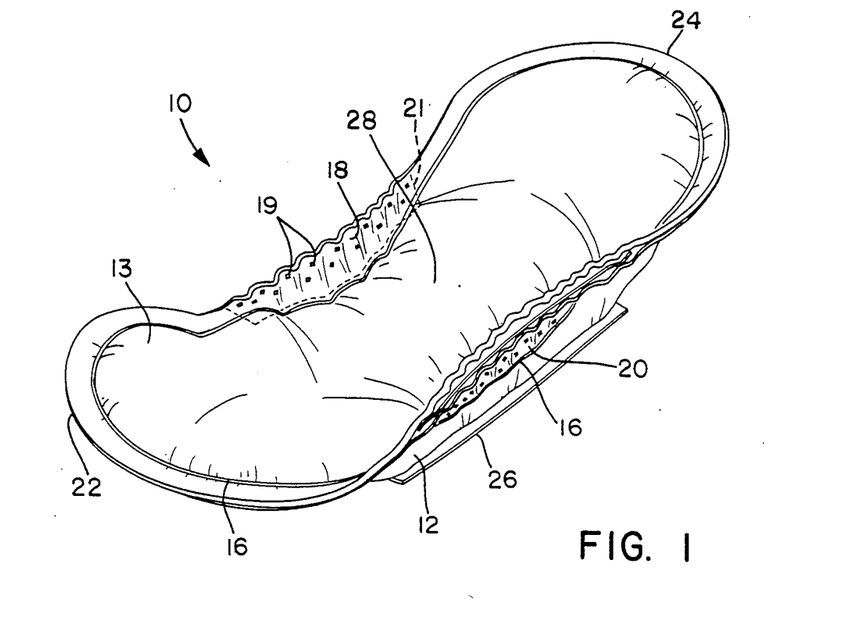
FIG. 1 is a perspective view of a pad in accordance with the invention.

As illustrated in FIG. 1, pad 10 is composed of a liquid-impermeable backing 12 that forms a basin shape. The body-side material 13 lines the interior of the basin. The impermeable member 12 and body-side permeable member 13 are joined at a seal line 16 extending around the periphery of the pad 10. Upstanding walls 18 and 20 are located in the middle portion of the long sides of the pad 10. The walls at their top are about the same width as the absorbent. The ends 22 and 24 are rounded. The pad is provided with a removable peel strip 26. The peel strip 26 may be removed to expose adhesive for attachment to an undergarment. The center portion 28 is somewhat raised up to about the height of the walls 18 and 20. The ends 22 and 24 are raised from the middle portion of the pad to form a bowed basin that will conform to the pudendum of a woman. The raised center portion 28 will generally be located near the vaginal orifice and urethral orifice.

Figure 2:
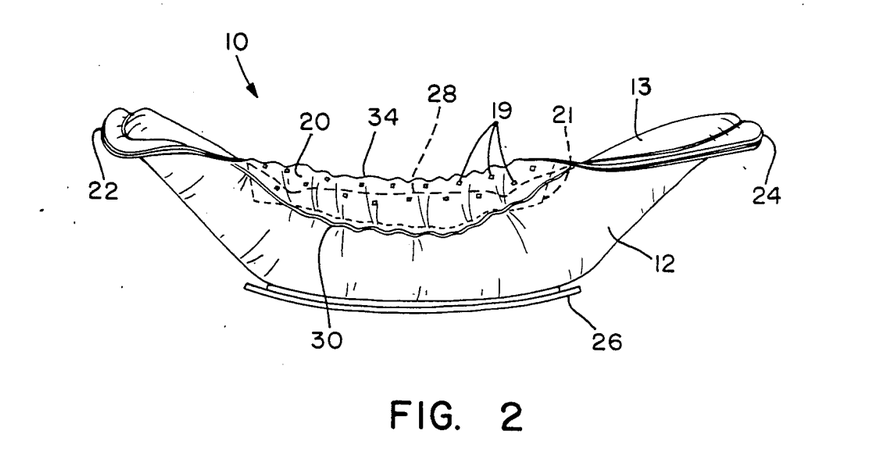
FIG. 2 is a side view of the pad of the invention.

FIG. 2 is a side view of the pad 10 of FIG. 1. The side view illustrates the peel strip 26 fastened to the bottom of basin 12. It also illustrates that the body side of the liner 13 is raised above the level of basin 12 at ends 22 and 24. Seal line 30 is where the body-side liner 13 and basin 12 have been joined; the joining of the body-side liner and the basin may be accomplished in several ways, such as adhesively or by ultrasonics. The seal line extends to the ends (note numeral 16 in FIG. 1). It is noted that the raised center portion of the body-side lining 28 extends almost to the height of the top 34 of wall 20.

Figure 3:
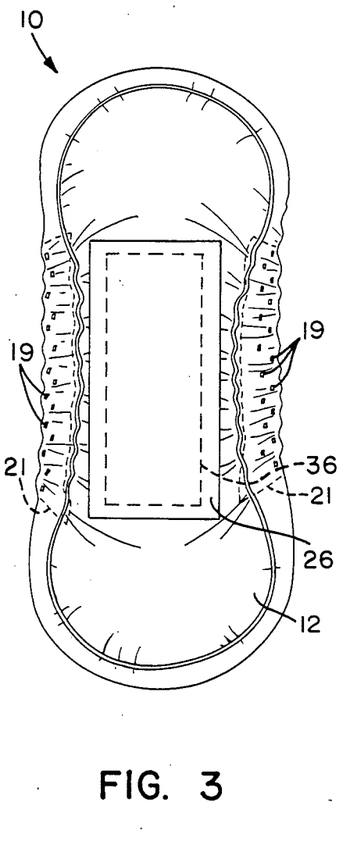
FIG. 3 is the bottom view of the pad of the invention.
Figure 4:
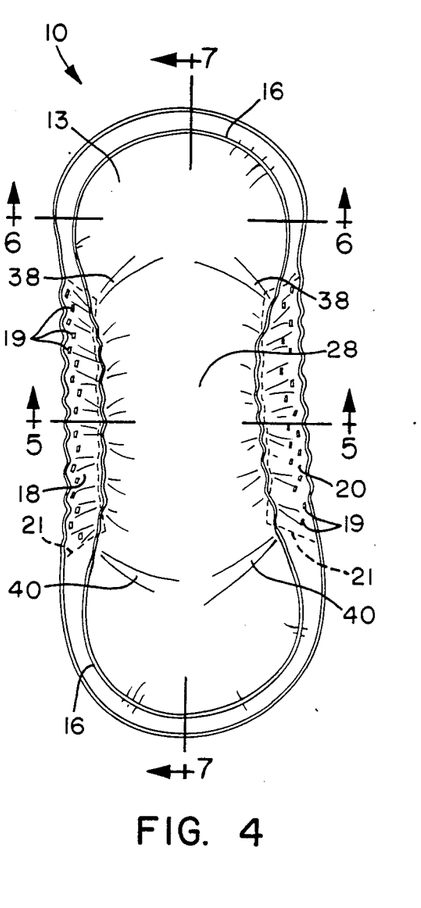
FIG. 4 is the top view of the pad of the invention.

FIG. 3 is a bottom view of the pad 10. The peel strip 26 covers the preferred single wide area of adhesive 36 or several lines of adhesive. FIG. 4 illustrates a top view of the pad of the invention. The pad is provided with a seal line 16 joining the liquid-impermeable backing 12 and the body-side liner 13. The line 16 is formed by ultrasonic sealing. However, it may be formed by other methods such as heat sealing or adhesives. The pad has rugosities 38 and 40 where the ends of the pad turn up. However, the center portion 28 is generally smooth. The walls 18 and 20 flair slightly outward as they extend upward from the seal line 16.

Figure 5:
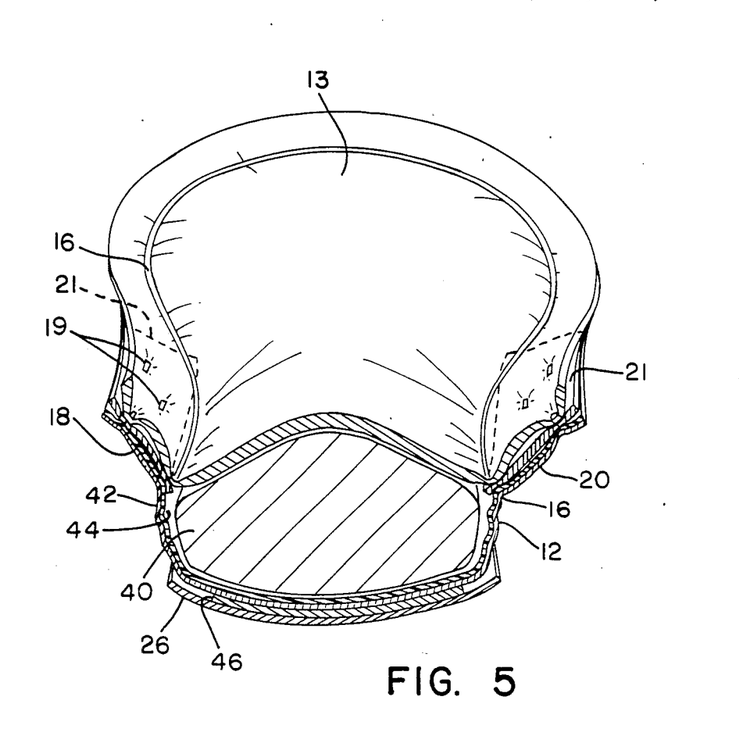
FIG. 5 is a section along line 5—5 of FIG. 4.
Figure 6:
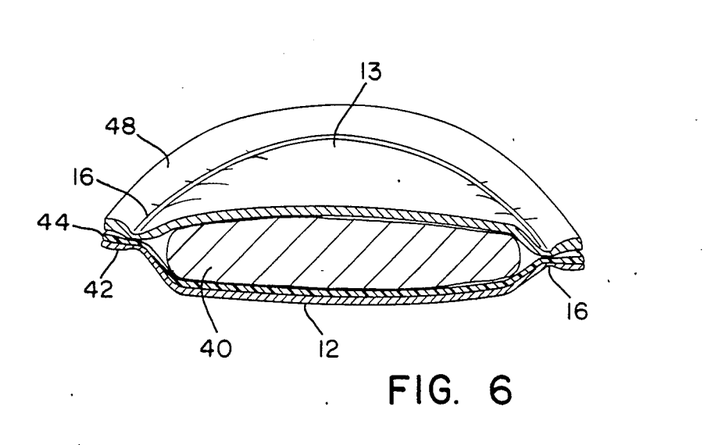
FIG. 6 is a section along line 6—6 of FIG. 4.
Figure 7:
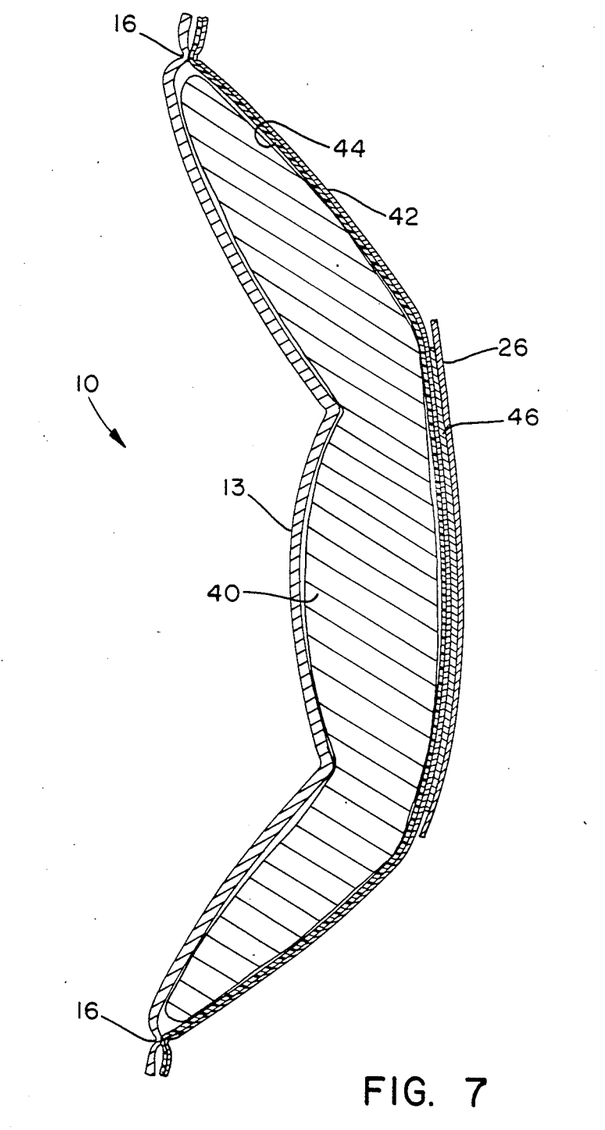
FIG. 7 is a cross-sectional view of the pad of the invention taken on line 77 of FIG. 4.

FIGS. 5, 6 and 7 are cross-sectional views of the pad taken on FIG. 4. FIG. 5 taken in the center portion of the pad across the width illustrates the absorbent 40 in the center portion of the pad forming an arched surface under permeable body-side layer 13. The walls 18 and 20 begin at seal line 16 where the cover 13 is bonded to the outer cover 12. Outer cover 12 is composed of two separate sheets formed into a single integral sheet 12. Sheet 12 is formed of a nonwoven outer sheet 42 and a liquid-impermeable polymer sheet 44 that are integrally connected. This provides the nonwoven surface that is soft and nonirritating to the skin. The peel strip 26 is located over adhesive 46 that is in a single wide area that will serve to hold the pad in place by bonding to the underwear of the wearer. FIG. 6 of a cross section taken at the wide portion near the end of pad 10 is somewhat wider than the center portion illustrated in FIG. 5. Further, the absorbent 40 is thinner than in the center portion and not as crowned or upwardly rounded. The view of FIG. 7 makes apparent the thicker middle portion of the pad's absorbent 40. The pad has the seal line 16 generally at about the vertical midportion of the absorbent 40. It is noted that the edges, such as 48, are loose and form a soft surface against the body.

Figure 8:
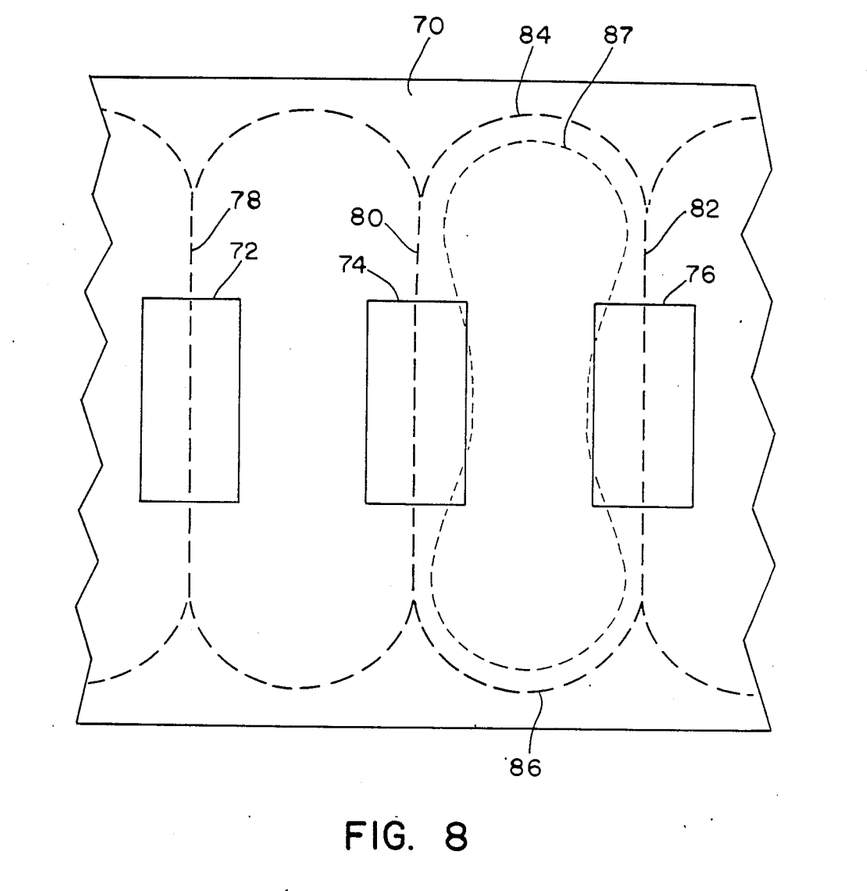
FIG. 8 illustrates a planar view of backing sheets of the invention with heat-shrinkable elastic in place.
Figure 9:
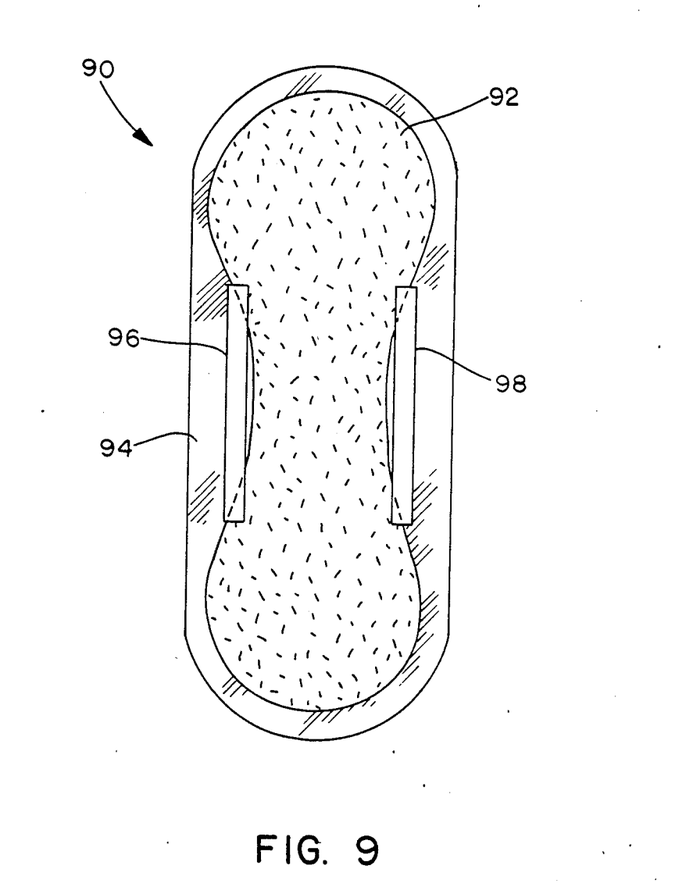
FIG. 9 illustrates in planar view another elastic placement system.

FIGS. 8 and 9 illustrate the formation of the products of the invention with two different optional placements of elastic material. In FIG. 8 a body-side sheet 70 is provided with several areas 72, 74 and 76 of material that will become elastic when it is heat shrunk. Lines 78, 80 and 82 represent cut lines between adjacent garments. The cut lines for the ends of the garments are represented by the lines 84 and 86. The heat-shrinkable material 74 is nonelastic when applied to the backing material, but upon heating, shrinks and becomes elastic. Line 87 represents where the absorbent would be placed. It is preferred that the pad be folded with the ends overlapping prior to applying heat to the side edges to shrink the elastic. The elastic also may be shrunk by application of heat to the flat pad. It is preferred to fold the garment and shrink the elastic by application of heat from the sides as this allows better application of heated air to the pad. FIG. 9 illustrates an alternate elastic location in which a pad 90, having absorbent 92 on impermeable backing 94, has applied thereto elastic strips 96 and 98. These elastics may be adhesively connected to the backing or body side liner while under tension, or they also may be heat-shrinkable elastic film materials.

Figure 10:
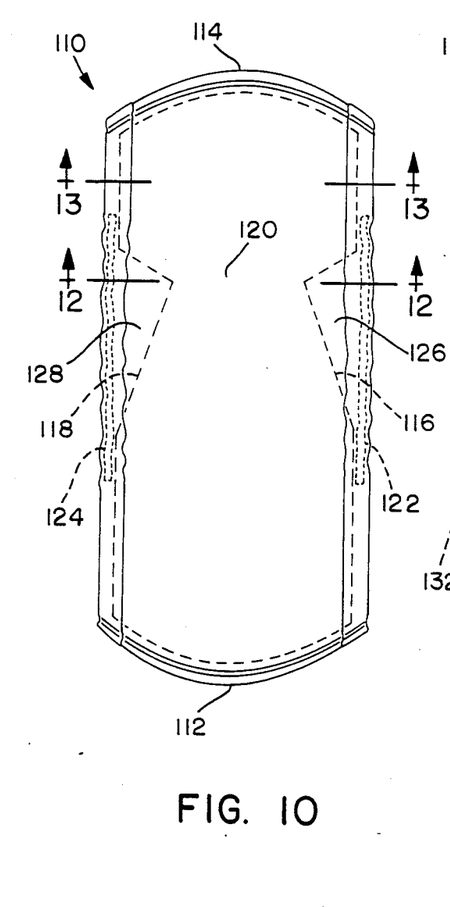
FIG. 10 illustrates an alternate pad of the invention having an irregular cutout of an hourglass shape.
Figure 14:
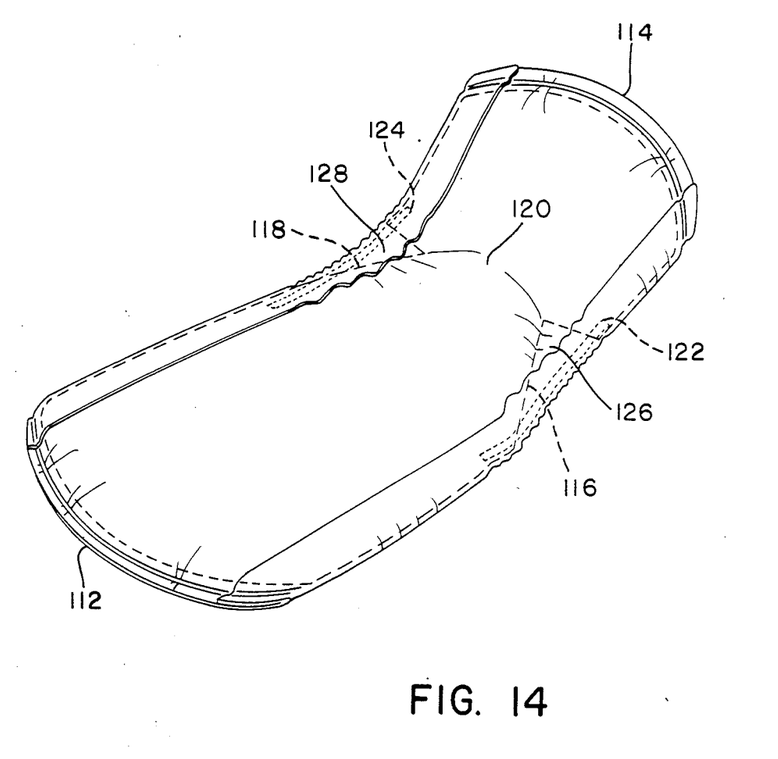
FIG. 14 is a view of the pad of FIG. 10 with the elastic in relaxed condition.

FIG. 10 is a view of an extended pad that is an alternate embodiment in accordance with the invention. FIG. 14 is a view of the pad 110 with the elastic in relaxed condition. In the pad illustrated in FIG. 10, there is formed a generally rectangular pad 110 having rounded ends 112 and 114. The pad has at 116 and 118 cutouts of the absorbent forming a narrowed crotch area 120. It is preferred that the cutout areas of absorbent be folded under to form a double thickness crotch area 120. There is elastic 122 and 124 placed in the flap or wing area 126 and 128. The pad 110 is illustrated in extended condition, and the elastic will make the pad bow in a similar manner to the earlier illustrated pads when the elastic is released. The pad as illustrated in embodiment of 110 is somewhat wider and is more suitable for incontinence use than the earlier illustrated narrower pads. The pad of FIG. 11, 130, has a more dog-bone shape having larger cutout areas 132 and 134. The dog-bone shape generally differs from the hourglass shape in that the narrow portion is elongated more for the dog-bone shape than in the hourglass shape.

Figure 12:
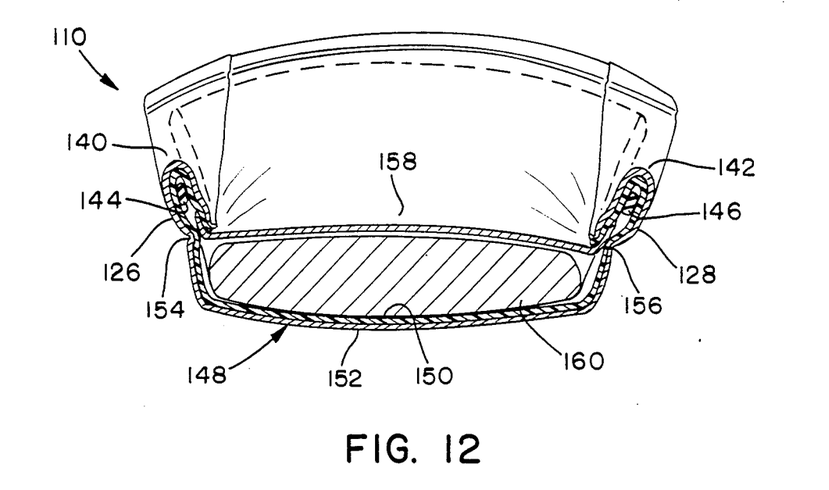
FIG. 12 is a cross section of the pad of FIG. 10 at the narrow portion.
Figure 13:
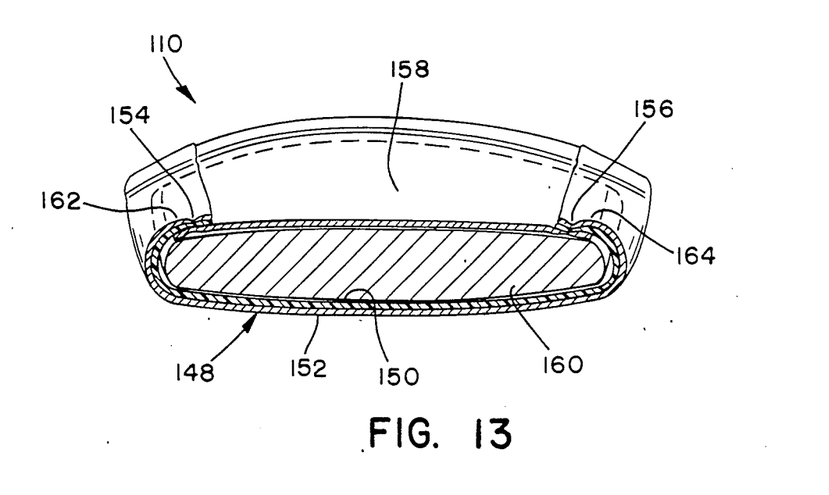
FIG. 13 is a cross section of the pad of FIG. 10 at a location near the end.

FIGS. 12 and 13 are cross-sectional views of the pad in accordance with the embodiment of FIG. 10. It is noted that the cross section of FIG. 12 is illustrated in the condition of the elastic being relaxed although FIG. 10 illustrates it in the stretched condition. As illustrated in FIG. 12, the flaps 126 and 128 have as the elastic contracted raised to form walls 140 and 142. The elastic strips 144 and 146 are in the upper portions of the upstanding walls. It is noted that the sheet 148 forming the liquid-impervious baffle or outer covering is formed of two layers—an impermeable polymer layer 150 on the inner side, and a cloth-like cover 152 integrally joined to it on the outside and extending up over the raised walls 140 and 142. The outer cover is ultrasonically or adhesively connected at 154 and 156 to the permeable body-side member 158. The absorbent 160 in pad 110 is a single layer of absorbent of generally uniform thickness. However, the absorbent could be formed with a thicker center portion as illustrated in the earlier preferred embodiments.

FIG. 13 is a cross-sectional view in the non-elasticized portion. This portion is generally planer even in the elastic-relaxed condition as there is no elastic in this portion. The pad as illustrated has the impermeable backing member 148 overlapping the absorbent 160 in areas 162 and 164. The advantage of the cloth-like outer surface of the backing material is that it is less likely to irritate where it contacts the skin of the wearer.

Figure 11:
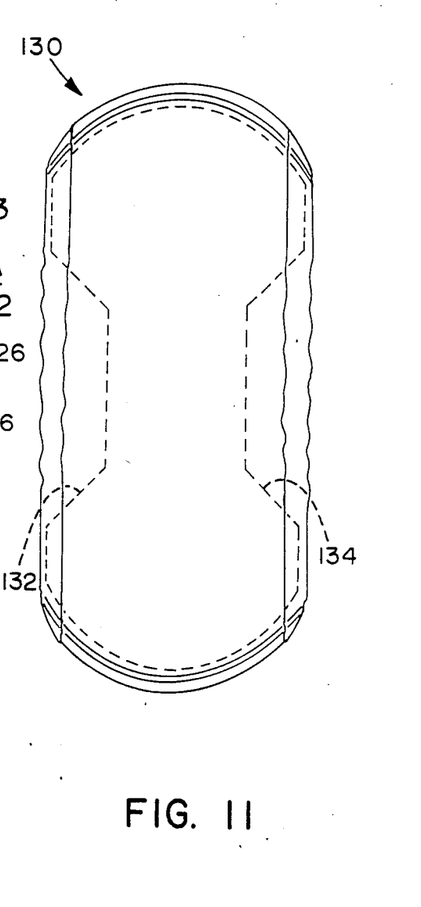
FIG. 11 illustrates an alternate embodiment of the invention having a generally dog-bone shape absorbent.

Other variations of the embodiments of FIG. 10 and 11 could include the folding under of partially cutout flaps of absorbent material to form a double thickness center portion. Other embodiments could include the addition of a second layer in the middle center portion in order to form increased absorbency.

In other embodiments in accordance with the invention it is possible that a superabsorbent material could be added to the pad to increase the absorbence in certain areas without increasing the absorbent thickness.

The absorbent materials used in the instant invention may be any absorbent material that will absorb bodily exudates such as catamenial fluids or urine. Suitable for such uses are absorbents of wood fluff, rayon, cotton and meltblown polymer such as polyester or polypropylene or coform. Coform is a meltblown air-formed combination of meltblown polymer such as polypropylene with absorbent staple fibers such as cellulose. A particularly-preferred material has been found to be wood fluff as it is low in cost, relatively easy to form and has good absorbency. The absorbent may be formed in a single contoured layer such as illustrated in the drawings, or it may be formed in two stages with an extra layer added to a base layer in the center area where greater thickness was desired.

The outer liquid-impermeable covering may be any desired material. Typical of such materials are polymer sheets of polypropylene, polyethylene or combinations thereof. Particularly preferred are composite material of a polymer and a nonwoven fabric material. The composite sheets are generally formed by extrusion of the polymer onto the spunbounded web to form an integral sheet. This material is preferred as the outer fabric surface is not irritating to the skin of the wearer. The walls of the pad of the instant invention generally extend up into the crease between the legs and the pudendum of the wearer. Therefore, the outer wall portions may come in contact with the legs of the wearer and should provide a comfortable nonirritating feel.

The body-side material may be any suitable permeable member. Typical of such materials are nonwovens, tissues, perforated polymer sheets, and composites of these materials. A particularly-preferred body-side material has been found to be a composite of a spunbonded polypropylene web bonded to a layer of staple fibers of polyester or polypropylene. The bonding is in small areas of ultrasonic sealing. The cover is preferred as it has a cushioned feel. This material is described in U.S. Pat. No. 4,397,644—Mathews et al.

The gathered portion forming the wall of the pad may be formed by any of several means. The gathered portion at the side of the pad of the invention generally is formed by the use of elastic. Any suitable elastic may be utilized. Heat-shrinkable elastics may find advantage in some formation methods in that the elastic may be applied in a nonelastic state as a film which becomes elastic upon heating. The heat-shrinkable material also has the advantage that it may be utilized on the entire flap with relative ease of formation. The material may be applied in a rectangular form, but when heating takes place from the body side of the pad, the absorbent will insulate any heat-shrinkable material from heat applied such that it will not shrink and only the area in the exposed flap will shrink. When normal elastics are utilized, the elastic generally is applied as an elongated strip that is glued in place while under tension and then allowed to relax. Such materials and processes for their application are well known in the art. Exemplary of heat shrinkable elastics are those of U.S. Pat. No. 3,912,565—Koch et al., U.S. Pat. No. 3,639,917—Althouse and U.S. Pat. No. 3,819,401—Massengale.

As an alternative embodiment, rather than the use of an impermeable polymer film backing with elastic in place, the pad of the invention may be formed from a moldable plastic foam material that is liquid impervious and soft to the wearer. The material would be molded with gathers in the wall portion so as to allow the pad to conform to the body of the wearer. Such a pad would not require elastic as it would be molded in the container shape rather than having the contraction of the elastic form the backing material into the desired container. A suitable foam material is a polyethylene-polyvinyl-acetate foam that may be vacuum and thermally molded to shape and then has the absorbent and body-side liner placed therein.

The preferred pad of the invention is designed such that the wall portions extend into the crease at the sides of the female genital organs or pudendum. The length is designed so as to extend adequately, caudally and dorsally, to prevent leakage in those directions while fit to the body and not be uncomfortable or interfering with the fit of the clothes of the wearer. While human body sizes and shapes come in a variety of forms, and it is possible to make an almost infinite number of garments to satisfy all body sizes, it has generally been found that a garment with a certain range of dimensions is satisfactory. Generally the narrow width portion in the center of the long edges is between about 1 and about 3 inches wide for catamenial and incontinence devices. Preferred for catamenial use is a width of 2-3 inches for absorption without leakage. Generally the length of the pad measured on the longest dimension of the liquid-impermeable backing member is between about 6 and about 10 inches. A preferred length distance is between about 8 and about 9½ inches for comfort and good leakage protection.

The adhesive to hold the garment in place may be placed upon the pad in any desired arrangement including a series of narrow strips. Generally the preferred arrangement is with the adhesive formed in one strip. The band has a total width of between about 1 and about 1¼ inches and a length of about 4 to 6 inches.

The amount of absorbent within the structure may be any suitable amount to maintain the fluids that are intended to be entrapped. Further, a highly-absorbent material, such as a hydrogel superabsorbent, may be added to the absorbent to aid in holding of fluid material.

The method of sealing the permeable member to the liquid-impermeable backing member may be any suitable method that does not leave a hard, uncomfortable residue that would be annoying to the wearer. Typical of sealing methods are heat sealing and adhesive sealing. The preferred method for the instant invention is ultrasonic sealing on a line inward of the edge of the pad at the ends, leaving a loose flap of material extending about a quarter inch outward from the seal line. Ultrasonic sealing is preferred as it results in a neat line with no adhesive cost and less tendency to perforate the material than heat sealing. The preferred form for the absorbent of the invention is in an hourglass or dog-bone shape with a narrow portion in the middle. In the most preferred form, the absorbent is thicker in the narrow portion to provide added absorbency in this critical area. When a pad with less absorbent properties is suitable, a single thickness layer of absorbent may be utilized. The absorbent in the thick center portion is preferably between about 1.75 and about 3 times the thickness of the end portions. Alternatively a pad of generally uniform thickness may be utilized, but with a higher absorbency material in the center portion than at the ends. Higher absorbency may be achieved by using fibers of greater absorbency or by adding superabsorbents.

While the device of the invention finds primary use as an incontinent or catamenial device, it is possible the device could find a utility as a dressing for injuries to the ear, elbow, foot or other joints.

In describing the present invention, certain embodiments have been used for purposes of illustration; however, other embodiments or modifications within the spirit and scope of the invention will readily occur to those skilled in the art after reading of this disclosure. Also the center portion with raised walls could be used with a long incontinence pad of a loincloth type. For instance, the pad of the invention could be held in place by belts rather than an adhesive. Further, the pad could be held in place only by a tight garment rather than by adhesive strips. The invention is accordingly not to be limited to the specific embodiments illustrated but only in accordance with the appending claims.

We claim:

1. An elongated catamenial or mold incontinence pad curved to the body shape having relatively long sides and narrowed ends for absorption of bodily excretions comprising a liquid-impermeable backing member having generally parallel longitudinal sides, an hour glass shape absorbent inner member and a liquid-permeable body-side member, wherein said absorbent generally has a narrow center portion shape, said backing member extends beyond said absorbent and has side edges forming flaps in the areas where the narrower portion of the absorbent does not overlay said backing, said flaps being gathered thereby raising said flap to form a wall on each side of the narrower portion of said absorbent wherein the distance between said walls is about the width of the widest part of said absorbent, wherein said absorbent is 1.75-3 times thicker in the middle of said pad than at the ends, wherein elastic is coextensive with the flap and wherein said flaps extend upward from about the middle of the vertical height of the thickest portion of said absorbent.

2. The pad of claim 1 wherein said backing is adhered to said liner in the area adjacent said absorbent.

3. The pad of claim 1 wherein the gathering of said flaps is by elastic.

4. The pad of claim 3 wherein said absorbent in the center of said pad extends up to about the height of said walls.

5. The pad of claim 1 wherein said impermeable layer is a composite of a fibrous web and a polymer film.

6. The pad of claim 2 wherein said liner and said impermeable backing extend beyond the area where they are adhered to form a soft fringe at the ends of said pad.

7. The pad of claim 1 wherein said absorbent has an hourglass shape.

8. The pad of claim 1 wherein said absorbent has a dog-bone shape.

9. The pad of claim 1 comprising a feminine pad.

10. The pad of claim 1 comprising an incontinent pad.

11. The pad of claim 1 wherein said body-side member is generally coextensive with said backing member in the flap area.

12. The pad of claim 3 wherein said elasticized side edges are generally parallel.

13. The pad of claim 1 wherein said absorbent extends above said walls.

14. The pad of claim 3 wherein said elastic is at the outer edge of said wall.

15. The pad of claim 1 wherein the ends of said pad are generally planar.

16. The pad of claim 1 wherein said narrow center portion is between about 1 and about 3 inches wide.

17. The pad of claim 1 wherein said pad is between abut 8 and about 9½ inches long.

* * * * *